United States Patent [19]

Clark

[11] 4,082,846
[45] Apr. 4, 1978

[54] METHOD FOR TREATING PSORIASIS

[75] Inventor: Lealand L. Clark, Salt Lake City, Utah

[73] Assignee: University of Utah, Salt Lake City, Utah

[21] Appl. No.: 743,015

[22] Filed: Nov. 18, 1976

[51] Int. Cl.² .......................................... A61K 31/455
[52] U.S. Cl. .................................................. 424/266
[58] Field of Search ........................................ 424/266

[56] References Cited
PUBLICATIONS

Chemical Abstracts 53:1553c (1959).

Primary Examiner—Leonard Schenkman

[57] ABSTRACT

A method for treating psoriasis by the topical application of the hydrazide of isonicotinic acid (isoniazid) in a carrier base. Isoniazid is a known compound and has the structural formula as follows:

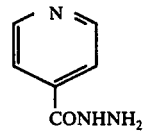

3 Claims, No Drawings

METHOD FOR TREATING PSORIASIS

BACKGROUND

1. Field of the Invention

This invention relates to the treatment of psoriasis and, more particularly, to a method for treating psoriasis by topically applying isoniazid in a carrier base to the psoriasis lesion.

2. The Prior Art

Psoriasis is a common but complicated, proliferative and inflammatory disease of the skin. Psoriasis is usually chronic though sometimes acute and affects about two to three percent of the United States population. About 500,000 of these victims of this painfully disfiguring disease experience serious difficulties finding anything resembling a normal life. Additionally, a severe psoriatic arthritis may totally incapacitate the patient and make employment almost impossible. Extensive involvement of the skin, of the feet and hands may make weight-bearing intolerable and simple motions of the digits next to impossible. The large prominent red plaques on the skin and the continual sloughing of scales are a source of constant embarrassment because of misunderstanding or even ridicule on the part of those who behold the marred skin surface of the carrier. Accordingly, psoriasis is not just a skin disease; it is a highly personal tragedy.

Psoriasis is unusual in children but relatively common at any age after puberty. Genetic factors are presently considered to be of prime importance in transmission of the disease, but environmental agents appear to also play an important role. For example, certain psoriatic lesions unquestionably have been produced by some blunt mechanical trauma, possibly of a chronic nature. For example, the mechanical trauma can result from carrying a heavy suitcase, ironing, gripping a steering wheel or swinging of a golf club. On occasion, the mechanical trauma may be occupational in origin, such as in a seamstress or one working with heavy cardboard boxes. This latter sequence is well known as Koebner's phenomenon.

The early stage eruption of psoriasis may be non-specific in appearance. In fact, early psoriasis is often confused with a variety of skin diseases such as drug eruptions, dermatitis, fungus disease, insect bites and chicken pox. Early lesions are asymptomatic although some patients complain of mild pruritus. The initial lesion is an erythematous papule which may progress to pustulation, accounting for the confusion with chicken pox. Soon after the erythematous papules, the characteristic papulosquamous plaque appears. The typical psoriatic eruption consists of erythematous, scaling plaques of variable size. The lesions are, in most cases, symmetrical.

Clinically, the scale is distinctive, silvery and luxuriant in its pristine, untreated state. Underneath is a dull red surface which, upon removal of the scale, may show fine capillary bleeding points. Always sharply limited in border and frequently clearing in the center, psoriasis may come in any size and the scale, may, in turn, range from being absent to extremely thick.

Psoriasis, in addition to being an inflammatory disease, is a benign hyperplastic disease of the skin. Importantly, epidermal cells in areas of skin involvement have a very rapid rate of replication. The mitotic index of the germinative cell population per unit length of involved epidermis is increased, and there is a reduced epidermal cell transit time, or epidermal cell "turnover" time in involved areas. Accordingly, the epidermis of the psoriatic lesion grows very fast (about ten times normal rates) and sheds large amounts of scale. This is one of the key factors in the pathology of the disease.

In view of the foregoing, the principal thrust of the treatment protocol centers around use of antimetabolites or nicotinamide antagonists, such as the topical application of Methotrexate, and folic acid antagonist; Azaribine, an orotidylate decarboxylase inhibitor (triacetyl-6-azauridine); Hydroxyurea; 6-aminonicotinamide; and systemicly with mycophenolic acid. The first three drugs are antimetabolic agents and have been reported effective in producing remissions in patients with severe recalcitrant disease.

However, all of these drugs have major side effects and can be given only in very severe cases and under extremely careful supervision by those experienced in their use. In many instances, some of the adverse effects of these drugs are worse than the psoriasis particularly when using antineoplastic agents.

Other topical agents are generally quite safe, and with diligent, continuous application can be effective. The oldest and most widely used topical agent is crude coal tar in conjunction with exposure of the psoriatic lesion to ultraviolet light. Other topical agents which have been found useful are anthralin, topical glucocorticosteroids, ammoniated mercury, and vitamin A acid.

In view of the foregoing what is needed in a method for treating psoriasis by the topical application of a suitable compound to the psoriatic lesion. It would be an even still further advancement in the art to provide a known compound for which extension physiological studies have been made and use the same in the method for treating psoriasis. Such a discovery is disclosed herein.

BRIEF SUMMARY AND OBJECTS OF THE INVENTION

The present invention relates to the novel discovery that a tuberculostatic drug, isonicotinylhydrazine (isoniazid), is surprisingly effective for treating psoriasis. The method of the invention is practiced by topically applying the isoniazid to the psoriatic lesion. Preferentially, the isoniazid is mixed with a carrier such as hydrophilic ointment in amounts ranging between 0.5% and 10%, by weight. Topical ioniazid is a vasodilator and this effect can be, selectively, controlled by combining a known vasoconstrictive agent with the isoniazid.

It is, therefore, a primary object of this invention to provide improvements in the method of treating psoriasis.

An even still further object of this invention is to provide a method for treating psoriasis by topically applying isoniazid to the psoriatic lesion.

An even still further object of this invention is to provide a method for treating psoriasis by applying isoniazid in combination with a vasoconstrictive agent to balance the vasodilation action of the ioniazid.

These and other objects and features of the present invention will become more fully apparent from the following description and appended claims.

DETAILED DESCRIPTION OF THE PREFERRED EMBODIMENTS

Isoniazid is the hydrazide of isonicotinic acid and has the following structural formula:

Isoniazid is well known as a tuberculostatic drug and an odorless, while crystalline powder that is freely soluble in water. The pH of a 1% solution is 5.5 to 6.5.

Any chemical change in isoniazid leads to a reduction or loss of efficacy toward tuberculosis. Substitution in the pyridine ring, reduction of the ring, alkylation or acylation of the hydrazine nitrogen, or condensation with aldehydes or ketones results in a decrease in tuberculostatic activity.

Principally, the thrust of the research associated with isoniazid is directed toward its superior tuberculostatic activity. The precise mechanism of the tuberculostatic action of isoniazid is presently unknown. However, several possible modes of the tuberculostatic and tuberculocidal action in vitro of isoniazid have been suggested. For example, it has been postulated that the drug as an effect on lipids, the content of which is high in the walls of tubercle bacilli and which may be essential for their viability. Exposure to isoniazid leads to a loss of acid fastness and a decrease in the quantity of methanol-extractable lipid of the microorganisms.

The drug has also been shown to inhibit the initial stages of DNA synthesis; this is followed by cessation of synthesis of RNA. It has also been suggested that isoniazid first blocks nucleic acid synthesis and that this is followed by inhibition of the production of proteins and biosynthetic enzymes in the mycobacterial cell. The quantity of NAD in sensitive bacterial cells is reduced by the drug; this is not related to the concentration of isoniazid or the duration of exposure to it. An effect on glycolysis, leading to decrease in carbohydrate content of Mycobacteria, has also been demonstrated.

It has been further suggested that isoniazid's primary activity is combination with an enzyme specific for susceptible tubercle bacilli so that a molecule that is related to production of pigment, under conditions in which the dug is not lethal, is simultaneously displaced. Reactions of the pigment precursor or the modified enzyme, in the presence of appropriate substrates, are thought to produce alterations in the metabolism of proteins, nucleic acids, carbohydrates, and lipids.

Surprisingly, it has been found that the topical application of isoniazid to a psoriatic lesion is a very effective method for treating psoriasis. Instead of being administered orally or parenterally as in the treatment of tuberculosis, the isoniazid is effective as a topical application. This is a surprising and unexpected result particularly in view of the tendency for a patient to develop a pellagra-like skin eruption during treatment with isoniazid. For example, a literature report discusses a 30-year-old man with a diagnosis of tuberculosis meningitis. The patient was under treatment with intramuscularly and intrathecally administered streptomycin sulfate, ethionamide, and Isoniazid. Although his general condition improved his mental and neurological damage was profound. He became totally blind and had gross weakness and incoordination of his lower limbs. He also became very depressed and apathetic with a significant loss of appetite and weight. The degree of metal impairment was such that a diagnosis of organic dementia was made by a consultant psychiatrist and it was assumed that this was because of organic brain damage resulting from vasculitis associated with tuberculous meningitis.

The most plausible diagnosis was that there was a pellagra-like reaction to the isoniazid with acneiform horny plugs as additional supporting evidence. It was subsequently established that acetylation of isoniazid was slow in the patient and he would, therefore, be more likely to suffer from its side effects than individuals who excrete the drug more rapidly. It was considered unsafe to discontinue therapy with isoniazid, and, since a rash had not responded to a variety of other topically applied medications, the possible beneficial effect of topically applied niacinamide was investigated. A cream was prepared as 1% niacinamide in cetomacrogol 1000 and applied twice daily. Within seven days a substantial improvement was observed including the patient's general overall condition although no change in systemic medication had been made. Whereas for five months the patient had led a vegetable-like existence, during the period of treatment with niacinamide he became more alert, even talkative, and his eating habits improved substantially so that he gained weight clearly making the previous diagnosis of permanent organic dementia no longer applicable.

From the foregoing, it is clear that the method involving the topical application of isoniazid to a skin disease such as psoriasis is not obvious but exhibits surprisingly beneficial results in the treatment of psoriasis.

Preferentially, the isoniazid is dispersed in a suitable carrier such as a hydrophilic ointment U.S.P. so as to assure the application of a suitable dosage of isoniazid to the psoriatic lesion. The Isoniazid is mixed with a hydrophilic ointment U.S.P. in a ratio of about 10.0%, by weight, and applied topically to the psoriatic lesion several times a day. Treatment is continued as necessary to effect and maintain clearing.

Topical isoniazid is a vasodilator and can be a nuisance particularly for light-skinned patients. However, it has been found that the vasodilation characteristics can be easily controlled with a topical steroid such as betamethasone valerate which exhibits high levels of vasoconstrictive activity. Other vasoconstrictive steroids include Triaminolone Acetonide and Fluocinonide. These steroids are selectively included with the isoniazid in amounts ranging about 0.025% to 0.5% by weight.

Tests were conducted as controls to demonstrate the treatment with the hydrophilic ointment U.S.P. or the topical steroids alone in the absence of isoniazid was ineffective toward treating psoriasis.

The following restrictive examples are given by way of illustration of the method of this invention without limiting the scope of the claims therefor.

EXAMPLE NO. 1

Patient No. 1 exhibited classical psoriasis lesion. Treatment was commenced with 1% isoniazid, by weight, in hydrophilic ointment, U.S.P. The isoniazid was applied four times per day for six days and effected complete clearing of the psoriatic lesion. Continued application was found necessary to maintain clearing.

EXAMPLE NO. 2

Patient No. 2 was used as a control to test the efficacy of the hydrophilic ointment, U.S.P., alone in treating psoriasis. The hydrophilic ointment, U.S.P., was applied three time a day for 21 days and there was no clearing exhibited in the psoriatic lesion.

Subsequently, the psoriatic lesion of Patient No. 2 received a topical application of 5% isoniazid in hydrophilic ointment, U.S.P., which was applied three times a day for 21 days and obtained clearing of the psoriatic lesion. Continued application was found necessary to maintain clearing.

EXAMPLE NO. 3

Patient No. 3 was a 14-year-old female with a classical example of a psoriatic lesion on the right knee. The psoriatic lesion was treated by the topical application of 1% isoniazid in hydrophilic ointment U.S.P. Clearing was obtained after seven days of treatment and the patient remained clear for 90 days without further treatment.

EXAMPLE NO. 4

Patient No. 4 was used as a control to test the efficacy of betamethasone valerate alone as a composition for the treatment of psoriasis. Betamethasone valerate (0.1%, by weight) was applied three times a day to a psoriatic lesion and after 12 days had not effected clearing of the lesion. The only noticeable difference was a reduction in the redness associated with the psoriasis through the vasoconstrictive activity of the betamethasone valerate.

Isoniazid (5.0% by weight) was mixed with betamethasone valerate (0.5% by weight) in hydrophilic ointment, U.S.P., and applied three times a day. After 12 days of treatment complete clearing of the psoriatic lesion was obtained.

EXAMPLE NO. 5

Fifteen patients having psoriatic lesions on various parts of the anatomy were treated with various proportions of isoniazid in a hydrophilic ointment U.S.P. and in combination with different types and strengths of steroids. A control was established by having the patient treat certain portions of the psoriatic lesion with the steroids and/or hydrophilic ointment, U.S.P., only. A comparison of the medication results and the control results are set forth in Table I below.

It should be particularly noted also that each of the patients in this example had previously been unsucsessfully treated with various compounds and combinations of compounds including, for example, the topical application of cortisone creams, betamethasone valerate (0.1%), halcinonide (0.1%), traminolone acetonide cream (0.1% and 0.5%), prednisone, fluorocinoide, and hydrophilic ointment U.S.P., alone, as a control. Additionally, certain patients were given intramuscular injections of triamcinolone acetonide.

Furthermore, two patients were misdiagnosed as athlete's foot and ringworm. The first patient was unsuccessfully treated with two fungicidal creams, miconazole nitrate and tolnaftate while the second patient was unsuccessfully treated with another funicide, clotrimazole (1.0%).

Importantly, regardless of the previous treatment protocol, the prior treatment technique for the psoriatic lesion was found to be unsuccessful to the extent that little or no clearing was obtained.

Each of the patients in Table I above were instructed to apply an effective amount of the medication as a cream topically to the psoriatic lesion three times a day. Most patients complied with this instruction although, on occasion, patients tended to forget or to be over zealous in their application of the cream. Regardless of the variations in the application technique, the novel method of this invention was found to be surprisingly effective toward clearing the psoriatic lesions.

The invention may be embodied in without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for treating psoriasis comprising the steps of:
    topically applying a composition containing about 0.5% to 10.0%, by weight of isoniazid in an effective amount to the psoriasis; and
    repeating the applying step as necessary to effect treatment of the psoriasis.

2. The method of claim 1 wherein the composition additionally contains 0.025% to 0.5% by weight of a topical steroid having vasoconstrictive activity.

3. The method of claim 1 wherein the composition is in the form of a hydrophilic ointment.

TABLE I

| | | COMPARISON OF THE EFFECTIVENESS OF TREATING PSORIASIS WITH AND WITHOUT ISONIAZID (INH) | | | |
|---|---|---|---|---|---|
| | | MEDICATION WITH INH | | | |
| TEST GROUP | NUMBER OF PATIENTS IN TEST GROUP | % INH in HYDROPHILIC OINTMENT | % STEROID | MEDICATION RESULTS (% CLEARING) | CONTROL RESULTS WITHOUT INH (% CLEARING) |
| A | 6 | 0.5% INH | 0.1% Betamethasone Valerate | 100% | 0-20% |
| B | 2 | 0.5% INH | 0.1% Triaminolone Acetonide | 85-100% | 0-20% |
| C | 3 | 1.0% INH | 0.1% Triaminolone Acetonide | 70-90% | 10-20% |
| D | 1 | 1.5% INH | 0.1% Triaminolone Acetonide | 80% | 10% |
| E | 1 | 5.0% INH | 0.1% Betamethasone Valerate | 100% | Less than 5% |
| F | 1 | 5.0% INH | None | 100% | No Visible Results |
| G | 1 | 10.0% INH | 0.1% Fluocinonide | 100% | No Visible Results (Discontinued after 3 days) |

The foregoing results of Table I clearly demonstrate that the isoniazid exhibits a superior effectiveness toward clearing psoriasis whereas the steroid and/or hydrophilic ointment, U.S.P., alone proved to be of little utility. Additionally, each patient should be accurately diagnosed for psoriasis to assure proper treatment with isoniazid.